United States Patent [19]

Schlosser

[11] 4,361,810
[45] Nov. 30, 1982

[54] ARRANGEMENT FOR MONITORING THE CONCENTRATION OF POTENTIALLY EXPLOSIVE SUBSTANCES IN GAS STREAMS

[75] Inventor: Wolfgang Schlosser, Germering, Fed. Rep. of Germany

[73] Assignee: Ratfisch Instrumente, Munich, Fed. Rep. of Germany

[21] Appl. No.: 184,889

[22] Filed: Sep. 8, 1980

[30] Foreign Application Priority Data

May 10, 1980 [DE] Fed. Rep. of Germany ....... 3017945

[51] Int. Cl.³ ............................................. G01N 27/00
[52] U.S. Cl. ............................................ 324/468; 422/54
[58] Field of Search ................. 324/464, 468; 422/54; 23/232 R, 232 E

[56] References Cited

U.S. PATENT DOCUMENTS 3,425,806 2/1969 Karmen .................................. 422/54
3,852,037 12/1974 Kolb ...................................... 422/54

*Primary Examiner*—Michael J. Tokar
*Attorney, Agent, or Firm*—Michael J. Striker

[57] ABSTRACT

An arrangement for monitoring the concentration of potentially explosive substances in gas streams includes a first flame-ionizer and a second flame-ionizer, both ionizers being accommodated in a common chamber which is maintained at a predetermined temperature, such as 180° C. A common conduit for supplying both ionizers with a fuel gas is provided in the arrangement. A common conduit for feeding both ionizers with combustion air is mounted in the arrangement. Each ionizer is provided with an individual conduit connecting the assigned ionizer with a respective drying chamber of a coating installation. A sample gas stream discharged from the respective drying chamber is fed into the assigned ionizer through a capillary pipe and passed through a flame produced in each ionizer. The electric current flowing between the electrodes in each ionizer shows the concentration of potentially explosive substance in gas streams being tested. The test data obtained in this arrangement are not affected by varying temperatures in the testing equipment.

13 Claims, 2 Drawing Figures

ARRANGEMENT FOR MONITORING THE CONCENTRATION OF POTENTIALLY EXPLOSIVE SUBSTANCES IN GAS STREAMS

BACKGROUND OF THE INVENTION

The invention relates to continuously monitoring the concentration of potentially explosive materials, such as hydrocarbon, in a number of separate gas streams used as samples discharged from gas containing equipment such as coating installations. More particularly, the invention relates to an arrangement for continuously monitoring the concentration of potentially explosive gases in gas streams by means of flame-ionizers where the concentration at a lower limit of explosiveness is monitored by ionization of gas samples.

The application of flame-ionization detectors for monitoring the concentration of hydrocarbon in gases or air is known in the art.

In such a detector or flame-ionizer, a fuel gas and a combustion supporting gas, such as air or oxygen are fed into a flame-ionizer chamber where they are burned to produce a flame. A gas stream of a substance to be tested containing a certain amount of hydrocarbon is supplied into the chamber, which gas stream passes through the flame of the ionizer which is provided with two electrodes supplied with direct voltage potential.

An electric current passing between the electrodes of the ionizer while a sample gas stream is passing through the flame is a function of the concentration of hydrocarbon in the sample gas stream. This current is approximately directly proportional to the amount of hydrocarbon atoms passing through the flame per time unit.

The flame-ionizers may be utilized, for example for monitoring the concentration of exhaust gases in motor vehicles, or also in the chemical or petro-chemical industry.

The flame-ionizers may be also employed in fields of technology where potentially explosive gases or vapors may be contained in the working gases and where the concentration of such potentially explosive gases should be monitored. One of such fields is coating installations.

Examples of such installations may occur in the electrical industry where wires are coated with insulating material, in the furniture industry where chipboard panels are covered with veneer, or in the construction industry where construction panels or frames are covered with synthetic plastic material; and also in the packing industry where sheets of carrier material are laminated at one side or at both sides thereof with a layer of synthetic plastic material.

In all of these applications, a coated material is passed through drying kilns or ovens in which solvents utilized in the coating materials are expelled in the form of vapors from the materials being dried during the drying process and must be removed. These solvent vapors may be highly explosive and are normally forwarded to after-burning equipment where they are burned, or else they may be directed to a solvent recovering installation.

In these applications care must be taken that the solvent vapors do not ignite, since this may lead to heavy explosions and to the destruction of the entire coating installation. To prevent this, the concentration of potentially explosive solvents in the vapors must be kept sufficiently low so that it cannot reach the so-called lower limit of explosion.

The drying installations known in the art normally include a number of individual drying chambers in which solvent vapors of different degrees of concentration evolve; all of these concentrations must be monitored to avoid the aforementioned undesirable results.

It has been proposed to monitor the gases or vapors evolving in the individual drying chambers by monitoring their heat content. The disadvantage of this method is that catalysts utilized in this method react relatively slowly and that the response time of such catalysts to changes in the concentration of the potentially explosive substances in the gases takes several seconds. Furthermore, this method has been found not to be sufficiently sensitive when only relatively small proportions of hydrocarbon are present in the gases to be monitored. Additionally, the catalysts are poisoned by certain substances contained in lacquer raw materials, such as heavy metals or sulfur-compound materials whereby the service life of the catalysts is reduced to only a few hours. Also, in the event silicones are present the catalysts or carrier material may become clogged by the silicone during the monitoring process.

It has been further suggested to withdraw a sample gas stream from each drying chamber and to pass these streams through a common pipe, by means of corresponding control valves, one after another to and through a flame-ionizer in which the concentration of hydrocarbons in the individual sample can be monitored.

This method has also been found disadvantageous in that it is evidently impossible to avoid discontinuous monitoring of the hydrocarbon concentration. Furthermore, only a portion of the time allotted for the monitoring of each separate sample is actually available for the monitoring operation, since the residual amounts of gas from the previous sample must be flushed out of the conduits and the flame ionizer before the next sample is admitted to prevent the occurrence of measuring errors due to commingling of two samples. When, for example, a new sample is admitted every ten seconds, then eight seconds are required to flush the previous sample out of the conduits and the ionizer and only two of the ten seconds are available for the actual measuring operation per sample. Even so, it is not possible in this method to exclude with absolute certainty that parts of the preceding sample may remain in the conduits and mingle with the next-following sample. Finally, the systems for switching the different sample-furnishing chambers into and out the sampling circuit requires relatively complicated and expensive electrical and/or electronic equipment, including data storages to provide quasi-continuous control.

SUMMARY OF THE INVENTION

It is therefore an object of the present invention to avoid the disadvantages of the prior art arrangements of the foregoing type.

More particularly, it is an object of the invention to provide an improved arrangement for continuously monitoring the concentration of potentially explosive substances in a plurality of gas streams.

Still another object of the invention is to provide an arrangement for continuously monitoring the concentration of potentially explosive substances, such as hydrocarbons, in gas streams leaving a number of drying chambers of a coating installation.

These and other objects are attained by means of an arrangement comprising means defining a chamber, a plurality of flame-ionizers in the chambers, means for supplying to each of said ionizers a requisite amount of fuel gas and means for supplying to each of said ionizers a requisite amount of combustion supporting gas to maintain a combustion flame at each ionizer, a plurality of conduits each connecting a respective one of said ionizers with a different source of gas to be monitored so that a stream of the gas passes through the flame of the ionizer for measurement of the concentration of the potentially explosive substance therein, and means for maintaining the chamber at a predetermined temperature.

The arrangement of the invention provides for continuous monitoring of the gases in each individual drying chamber of the coating apparatus, and for comparison of the measured results, without any disturbing influence which may be caused by different or varying temperatures of individual gas streams.

Flame-ionizers have a response time to changes in concentration of potentially explosive substances which is below 1 second. They thus enable appropriate corrective measures to be taken without delay when a change in the composition of a sample gas stream is detected, e.g. if the concentration of potentially explosive substance in a gas stream is found to approach the lower explosion limit. This rapid response time and the rapid corrective action enabled thereby to be taken, is especially important because it is desirable to operate near (e.g. within about 25%) of the lower explosion limit, in order to keep the additional energy required for afterburning at the lowest possible level.

Finally, the invention makes it possible for gases or vapors having hydrocarbon concentrations at or below the level which is permissible to discharge to the atmosphere, to be directly vented to the atmosphere.

Preferably, the temperature in the chamber accommodating the flame-ionizer(s) is about 180° C., i.e. higher than the dew point of the sample gas or vapor being tested.

Means for supplying fuel gas to each of the ionizers may include a common conduit.

Means for supplying combustion supporting gas to each of the ionizers may also include a common conduit.

The respective electrodes of each of the flame-ionizers may be electrically connected to common sources of energy.

The fuel gas supplying means may include capillary pipes for feeding the fuel gas into the ionizers.

The combustion supporting gas supplying means may also include capillary pipes for feeding the combustion supporting gas into the ionizers.

The conduits connecting each ionizer to a respective source of gas to be monitored may include capillary portions for feeding the streams of gas into the ionizers.

The arrangement of the invention may further be provided advantageously located in the consumer flame-ionizer chamber, with regulating means to control the amounts of gas to be monitored of the combustion supporting gas and the fuel gas so that all these components are maintained at identical, uniform temperatures.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DESCRIPTION OF THE PREFERRED EMBODIMENTS

Figure 1:
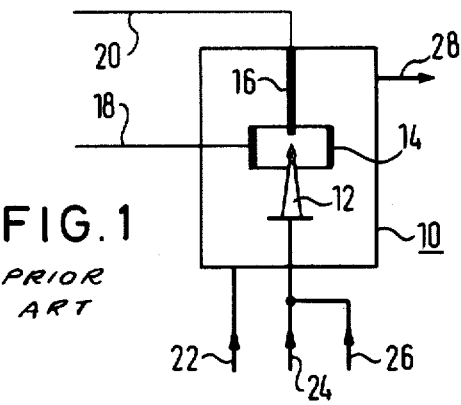
FIG. 1 is a schematic view of a prior-art flame-ionizer.

As shown in FIG. 1, a flame-ionization detector or flame-ionizer of the conventional type has a housing or chamber 10 in which a burner 12 is disposed. A ring-shaped electrode 14 and a rod-shaped electrode 16 are accommodated in the housing, which electrodes are electrically connected to a source of electric energy (not shown) by means of electrical conductors 18 and 20.

An oxidizing medium or combustion supporting gas such as synthetic air is supplied to the burner 12 through a conduit 22 while a fuel gas such as hydrogen is fed into the chamber 10 via a conduit 24 to produce a flame therein. A sample gas stream to be monitored enters the housing 10 through a conduit 26. The electrodes 14 and 16 are supplied with direct current and, due to the ionization of atoms of gases which takes place as the sample gas flows through the flame of the ionizer, an electric current flows between the electrodes. This current is a function of the proportions of hydrocarbons in the gas being monitored. A flame-ionization detector is disclosed in U.S. Pat. No. 3,718,430 and in German Pat. No. 26 26 232.

This arrangement permits linear measurement of the concentration of hydrocarbons from very small amounts, such as several ppm, up to very high percentage ranges of the concentration of potentially explosive substances. The response time of the arrangement is below 1 second. The electric current flowing between the electrodes of the ionizer is approximately directly proportional to the number of hydrocarbon atoms entering into the flame per unit time; this proportionality therefore also holds true with respect to the concentration of hydrocarbons in the gas relative to the lower explosion limit of different hydrocarbons.

The ionizer shown in FIG. 1 is also provided with an outlet 28 for discharging combustion gases from the housing 10.

Figure 2:
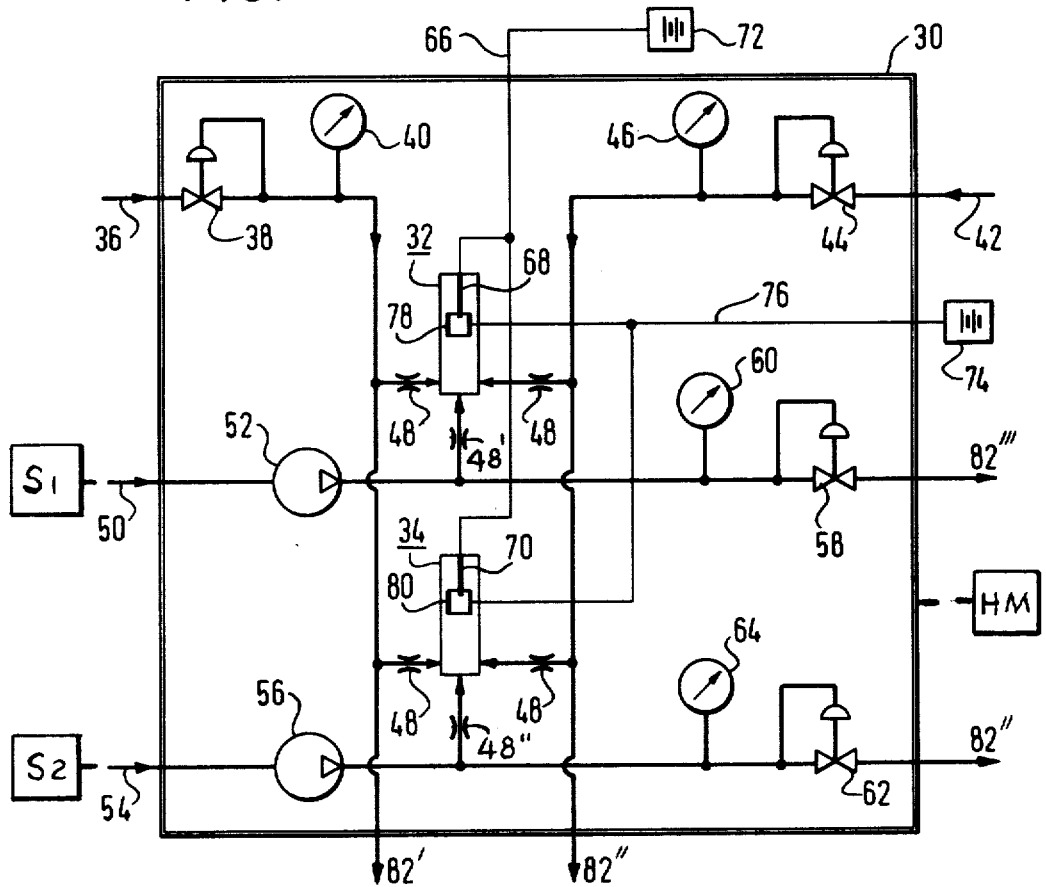
FIG. 2 is a schematic view of the arrangement for monitoring the concentration of potentially explosive substances in gas streams according to the invention.

Referring now to FIG. 2 which illustrates an arrangement according to the invention, the arrangement has a chamber 30 which is heated by heating means HM (not illustrated in detail) up to a substantially constant temperature of preferably about 180° C., which temperature is maintained during the ionization process.

The chamber 30 accommodates a first flame-ionization detector 32 and a second flame-ionization detector 34 (also called FID for convenience). It is to be understood that more than two FID's may be employed in the monitoring arrangement, if desired.

A common conduit 36 terminated with an end portion 82' is provided in the arrangement for supplying the ionizers 32 and 34 with combustion air. Pressure-regulating devices, including a pressure-regulating valve 38 and a manometer 40, are placed in the conduit 36. A fuel gas such as hydrogen is supplied to the ionizers 32 and 34 through a common conduit 42. The conduit 42 is terminated with an end portion 82". Pressure of the fuel gas in the conduit 42 is adjusted by means of a pressure-regulating valve 44 and a manometer 46 located in the conduit 42.

A conduit 50 is provided in the arrangement which serves to connect a first source S1 of gas to be tested with the ionizer 32. This source may be one of the drying chambers of a coating arrangement which was discussed above. The conduit 50 is terminated with an end portion 82'''. A pressure-regulating valve 58 and a manometer 60 are placed into the conduit 50. A requisite amount of a first sample gas stream is supplied to the ionizer 32 through a capillary portion 48' of the conduit 50. Back pressure in the conduit 50 may be adjusted by means of valve 58 and manometer 60.

The second ionizer 34 is provided with a second conduit 54 which connects a second gas supply source S2 (e.g. a second drying chamber of the coating installation) with an inlet of the ionizer 34 for feeding thereinto a second sample gas stream to be monitored. The conduit 54 also has a capillary portion 48'' for supplying gas to be tested into the ionizer 34 and an end portion 84$^{IV}$.

A pressure-regulating valve 62 and a manometer 64 are located in the conduit 54 after capillary portion 48'' to adjust back pressure of gas flowing through the conduit 54.

It should be noted that fuel gas, and combustion supporting gas as well as gas being monitored, are fed into ionizers 32 and 34 through the respective capillary pipes designated as 48—48''. Excess amounts of gases are discharged from the chamber 30 through the end portions 82', 82'', 83''' and 82$^{IV}$ respectively.

Pumps 52 and 56 are mounted in the conduits 50 and 54, respectively, which pumps are located in the respective conduits before their capillary portions 48' and 48''.

The first ionizer 32 has a rod-shaped electrode 68 and a ring-shaped electrode 78 whereas the second ionizer 34 is provided with a rod-shaped electrode 70 and a ring-shaped electrode 80. The electrodes 68 and 70 are connected to each other by means of an electrical conductor 66 which is further connected to a voltage source 72 of e.g. 200 V. The electrodes 78 and 80 are connected to separate amplifiers (not shown) which in turn are connected by an electrical conductor 76 to a common voltage source 74, e.g. ±15 V.

Two half-ring electrodes may be installed in each ionizer instead of one-ring shaped and one rod-shaped electrode. In this case each of the half-rings is formed as a segment with an angle of e.g. 180°.

As is shown in FIG. 2, both (or all) ionizers are located in one common chamber and are provided with individual conduits connecting them with different sources of gas to be monitored. In this arrangement the ionizers, feeding pipes, capillary pipes and pressure-regulating means are all located together in the common chamber so that they are all maintained at the same temperature, whereby erroneous measuring and consequently wrong test data of gas concentrations (caused by varying temperatures) are excluded.

Both ionizers have a common combustion air supply and a common fuel gas supply. The respective electrodes of both ionizers are electrically connected to common voltage sources.

The individual sample gas streams discharged for example from individual drying chambers of a coating device, are separately directed into the respective ionizers, whereby each ionizer may be assigned to a respective different drying chamber or other source of sample gas or vapor.

The arrangement of the invention thus provides for the continuous monitoring of the hydrocarbon proportions in several gas sources to be supervised. It offers a very short response time but excludes errors in the gas concentration measurements caused by varying temperatures in the equipment.

It will be understood that each of the elements described above, or two or more together, may also find a useful application in other types of monitoring arrangement differing from the types described above.

While the invention has been illustrated and described as embodied in a monitoring arrangement it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An arrangement for continuously monitoring the concentration of potentially explosive substances, such as hydrocarbons, in gas streams, particularly for monitoring the concentration of substances in gas streams from coating installations, comprising means defining a chamber; a plurality of flame-ionizers positioned within said chamber; means for supplying to each of said ionizers a requisite amount of fuel gas and means for supplying to each of said ionizers a requisite amount of combustion supporting gas so that a combustion flame is maintained at each ionizer; a plurality of sample conduits each connecting a respective one of said ionizers with a different source of gas to be monitored so that a stream of the gas passes through the flame of the ionizer for measurement of the concentration of the potentially explosive substance therein; and means positioned outside said flame-ionizers and operated for maintaining said chamber at a predetermined temperature.

2. The arrangement of claim 1, wherein said predetermined temperature is 180° C.

3. The arrangement of claim 1, wherein said means for supplying fuel gas to each of said ionizers include a common conduit.

4. The arrangement of claim 3, wherein said means for supplying combustion supporting gas to each of said ionizers include a common conduit.

5. The arrangement of claim 4, wherein each of said plurality of flame-ionizers has a pair of electrodes which are electrically connected to common sources of electric energy.

6. The arrangement of claim 5, wherein said fuel gas supplying means include capillaries for feeding the fuel gas into said ionizers.

7. The arrangement of claim 6, wherein said combustion supporting gas supplying means include capillaries for feeding the combustion supporting gas into said ionizers.

8. The arrangement of claim 7, wherein said sample conduits include capillary portions for feeding the streams of gas to be monitored into said ionizers.

9. The arrangement of claim 8, further comprising means for regulating the amounts of gas to be monitored, of combustion supporting gas and of fuel gas being supplied into said ionizers.

10. The arrangement of claim 9, wherein said regulating means include first pressure-regulating means located in said combustion supporting gas supplying means ahead of said capillaries thereof and in said fuel gas supplying means also ahead of said capillaries thereof.

11. The arrangement of claim 10, wherein said regulating means further include pumps located in each of said sample conduits ahead of said capillary portions and second pressure-regulating means placed in each of said sample conduits after said capillary portions.

12. The arrangement of claim 11, wherein said first and second pressure-regulating means include pressure valves and manometers.

13. The arrangement of claim 9, wherein said supplying means, said sample conduits and regulating means for said supplying means and sample conduits are at least in part located in said chamber so as to be at temperatures which are at least substantially identical to one another and to the temperatures of said flame-ionizers.

* * * * *